United States Patent
Flake et al.

(10) Patent No.: US 8,763,150 B2
(45) Date of Patent: Jun. 24, 2014

(54) CORRELATING PRIVATE AFFINITIES

(75) Inventors: Gary W. Flake, Bellevue, WA (US);
Eric I-Chao Chang, Haiden District (CN); Jason Garms, Woodinville, WA (US); Abhiram G. Khune, Sammamish, WA (US); Darrell Leroy Blegen, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 0 days.

(21) Appl. No.: 12/487,020

(22) Filed: Jun. 18, 2009

(65) Prior Publication Data
US 2011/0055930 A1    Mar. 3, 2011

(51) Int. Cl.
*H04L 29/00* (2006.01)
*G06F 21/00* (2013.01)
*G06F 19/00* (2011.01)

(52) U.S. Cl.
CPC .............. *G06F 21/00* (2013.01); *G06F 19/322* (2013.01)
USPC ............. 726/27; 709/223; 709/229; 709/238; 715/739

(58) Field of Classification Search
CPC ............................... G06F 21/00; G06F 19/322
USPC .............. 705/10; 707/10; 709/223, 229, 238; 715/739
See application file for complete search history.

(56) References Cited

U.S. PATENT DOCUMENTS

| | | | |
|---|---|---|---|
| 6,629,100 B2 * | 9/2003 | Morris et al. | 707/10 |
| 6,745,178 B1 | 6/2004 | Emens et al. | |
| 6,782,370 B1 | 8/2004 | Stack | |
| 7,167,920 B2 * | 1/2007 | Traversat et al. | 709/230 |
| 7,200,592 B2 | 4/2007 | Goodwin et al. | |
| 7,249,182 B1 | 7/2007 | Heinonen et al. | |
| 7,269,578 B2 | 9/2007 | Sweeney et al. | |
| 2003/0078976 A1 | 4/2003 | Gordon | |
| 2005/0038876 A1 * | 2/2005 | Chaudhuri | 709/219 |
| 2005/0181803 A1 | 8/2005 | Weaver et al. | |
| 2006/0168059 A1 | 7/2006 | Chang et al. | |
| 2006/0277092 A1 * | 12/2006 | Williams | 705/10 |
| 2007/0153703 A1 | 7/2007 | Floyd | |
| 2007/0214249 A1 * | 9/2007 | Ahmed et al. | 709/223 |
| 2007/0245245 A1 * | 10/2007 | Blue et al. | 715/739 |
| 2008/0040475 A1 | 2/2008 | Bosworth et al. | |

(Continued)

OTHER PUBLICATIONS

/Landon P. Cox, Angela Dalton, Varun Marupadi/ Smokescreen: Flexible Privacy Controls for Presence-Sharing/2007 pp. 233-245.*

(Continued)

*Primary Examiner* — Brandon Hoffman
*Assistant Examiner* — Michael D Anderson
(74) *Attorney, Agent, or Firm* — Dave Ream; Sade Fashokun; Micky Minhas

(57) ABSTRACT

The claimed subject matter relates to an architecture that can leverage private affinities in order to facilitate or enrich relationships between people. In particular, the architecture can receive a profile associated with a user wherein the profile includes a set of private affinities that are cryptographically protected from public inspection. The architecture can decrypt and/or cryptographically compare a private affinity from the profile to an affinity in a disparate profile (associated with a disparate user) in order to identify a matching affinity. Once a matching affinity is identified, a message indicating such can be provided to the user along with a request to publish certain revealed information to the disparate user, possibly based upon a mutual exchange of commensurate information from the disparate user.

20 Claims, 11 Drawing Sheets

(56) References Cited

U.S. PATENT DOCUMENTS

| | | | |
|---|---|---|---|
| 2008/0243526 A1 | 10/2008 | Nance et al. | |
| 2009/0063691 A1* | 3/2009 | Kalofonos et al. | 709/229 |
| 2009/0125637 A1* | 5/2009 | Matuszewski | 709/238 |
| 2009/0299937 A1* | 12/2009 | Lazovsky et al. | 706/47 |
| 2009/0319436 A1* | 12/2009 | Andra et al. | 705/80 |

OTHER PUBLICATIONS

Li, et al., Tag-based Social Interest Discovery. In: WWW 2008 / Refereed Track: Social Networks & Web 2.0—Discovery and Evolution of Communities, Apr. 21-25, 2008, Beijing, China. ACM 978-1-60558-085-2/08/04. http://www.2008.org/papers/pdf/675-lia.pdf. Last accessed Sep. 3, 2008, 10 pages.

Takeda, et al. Discovery of Shared Topics Networks among People—A Simple Approach to Find Community Knowledge from WWW Bookmarks. http://www-kasm.nii.ac.jp/papers/takeda/00/pricai00f.pdf. Last accessed Sep. 3, 2008, 11 pages.

Jung, et al. Towards Semantic Social Networks. ftp://ftp.inrialpes.fr/pub/exmo/publications/jung2007a.pdf. Last accessed Sep. 3, 2008, 14 pages.

Diaz, et al. Improving CoP Knowledge Sharing: A CSCW Approach Based on Awareness http://ftp.informatik.rwth-aachen.de/Publications/CEUR-WS/Vol-74/files/FORUM_43.pdf. Last accessed Sep. 3, 2008, 4 pages.

Lomas, et al. Collaboration Tools, ELI Paper 2: 2008, Aug. 2008 http://net.educause.edu/ir/library/pdf/ELI3020.pdf. Last accessed Sep. 4, 2008, 11 pages.

Oracle Webcenter 11g http://www.oracle.com/technology/products/webcenter/pdf/owc_r11_datasheet.pdf. Last accessed Sep. 3, 2008, 3 pages.

* cited by examiner

CORRELATING PRIVATE AFFINITIES

BACKGROUND

Today, many services exist that are directed to establishing and enriching personal relationships. For example, many conventional websites or other services allow users to create personal profiles or spaces that upon access reveal information about the user. Oftentimes, users are able to post a variety of content and arrange it in any suitable manner. Most personal profiles or spaces include various affinities describing likes or interests associated with the user. As an additional feature, many conventional sites or services also provide some mechanism for matching people, generally based upon characteristics revealed in the public profile or space.

Most users of such conventional systems understand that any affinity (or other information) included in an associated profile or space can be viewed by any third party who accesses that profile. This situation can substantially serve as a chilling effect on self expression or at least result in a profile that is a less accurate or less comprehensive representation of the associated user. For example, an ambitious professional is not likely to divulge that he likes, say, comic books, even though quite true. Appreciably, certain affinities especially those relating to fringe interests, eccentricities, or topics about which there is a common misconception or very little mainstream familiarity or understanding are generally omitted rather than included in conventional descriptions. Typically, this is so because these affinities might be a source of shame or embarrassment or incur undue explanation. Thus, certain cautious or prudent users may forego detailing an affinity that is not politically correct or one that might easily be taken out of context by others or virtually any affinity that can be the source of the slightest bit of embarrassment or conflict with a desired image.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The subject matter disclosed and claimed herein, in one or more aspects thereof, comprises an architecture that can leverage a private affinity in order to facilitate or enrich personal relationships. In accordance therewith and to other related ends, the architecture can obtain a profile associated with a user as well as a profile associated with a disparate user. The profile can include a private affinity that is protected from public inspection, potentially by way of encryption or access control techniques. The architecture can compare the private affinity to a disparate affinity (either public or private) included in the disparate profile in order to identify a matching affinity that correlates with the private affinity.

The architecture can then generate a message for the user indicating that a matching affinity has been identified. In addition, the architecture can provide a request to publish to the disparate user certain revealed information, wherein the revealed information is included in the profile of the user. In some cases, the matching can be facilitated based upon an established history of communication between the user and the disparate user. Additionally or alternatively, the matching can be facilitated when the user and the disparate user are in close geographic proximity. Hence, it can be readily appreciated by the above examples that something new can be learned about an old acquaintance and new acquaintances can be introduced or engaged when they are, say, in the same room or general location. Thus, the architecture can provide numerous benefits for old acquaintances as well as new ones by selectively revealing information associated with matching affinities.

In addition, the architecture can provide a number of additional features or aspects. For example, the architecture can facilitate anonymous communication between the user and the disparate user. Moreover, based upon inherent relationships and/or available data sets, the architecture can incorporate or leverage a number of advertising opportunities that can be especially beneficial to users as well as advertisers. For example, the architecture can facilitate peer-to-peer delivery of advertisements, which can be much more successful traditional ad-delivery mechanisms. Furthermore, the architecture can leverage statistical correlations, potentially in an anonymous manner that can be of great benefit to advertisers yet with no privacy issues for users arising. In fact, users can be benefited by way of incentives, economic or otherwise, in exchange for ad-delivery or correlation feedback.

The following description and the annexed drawings set forth in detail certain illustrative aspects of the claimed subject matter. These aspects are indicative, however, of but a few of the various ways in which the principles of the claimed subject matter may be employed and the claimed subject matter is intended to include all such aspects and their equivalents. Other advantages and distinguishing features of the claimed subject matter will become apparent from the following detailed description of the claimed subject matter when considered in conjunction with the drawings.

DETAILED DESCRIPTION

Figure 1:
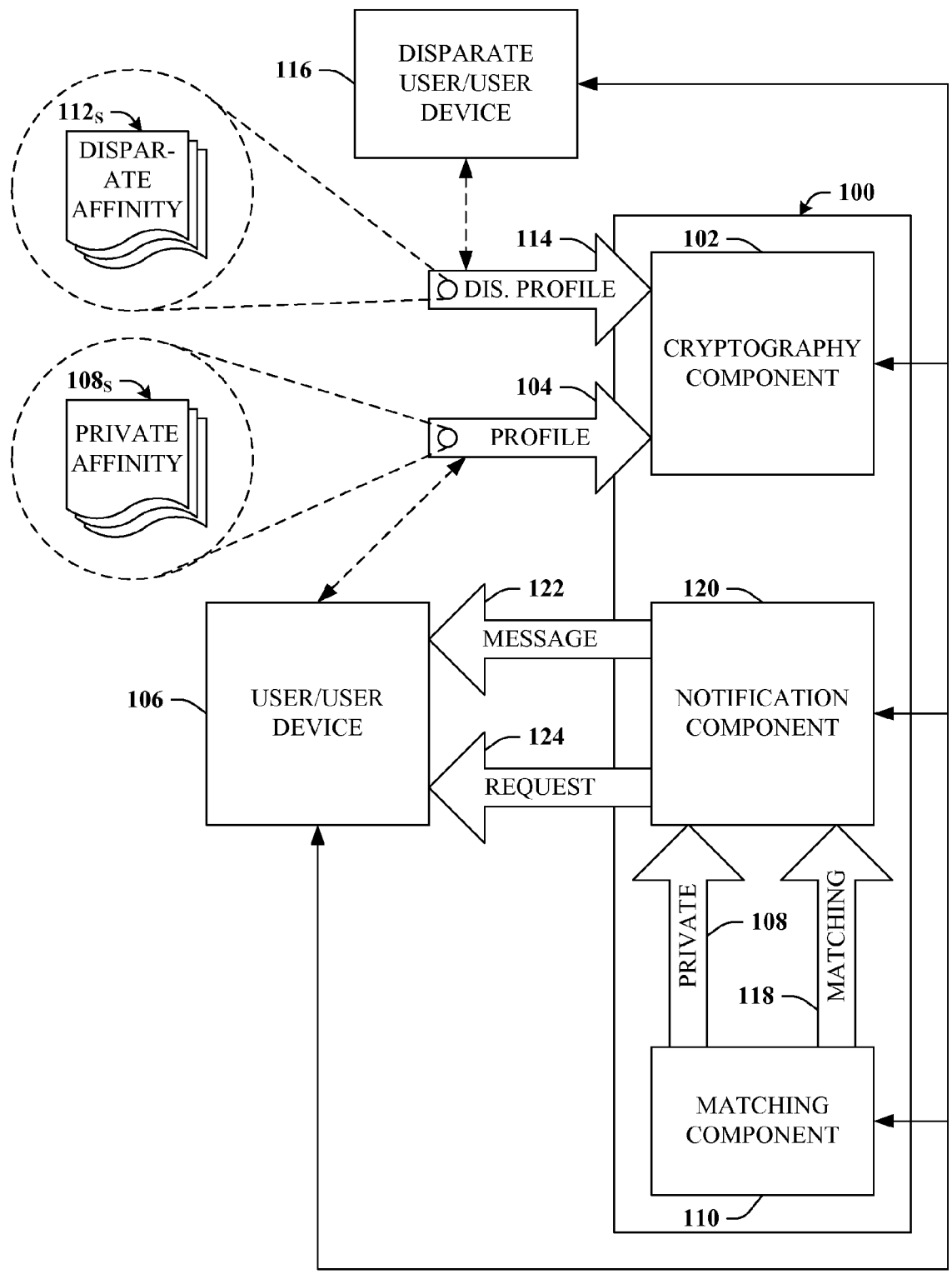
FIG. 1 illustrates a block diagram of a computer-implemented system that can leverage private affinities in order to facilitate or enrich personal relationships.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, well-known structures and devices are shown in block diagram form in order to facilitate describing the claimed subject matter.

As used in this application, the terms "component," "module," "system," or the like can, but need not, refer to a computer-related entity, either hardware, a combination of hardware and software, software, or software in execution. For example, a component might be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g. card, stick, key drive . . . ). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Moreover, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or." Therefore, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

As used herein, the terms "infer" or "inference" generally refer to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

Referring now to the drawings, with reference initially to FIG. 1, computer-implemented system 100 that can leverage private affinities in order to facilitate or enrich personal relationships is depicted. Generally, system 100 can include cryptography component 102 that can receive profile 104 associated with user 106. Profile 104 can include set 108$_S$ of private affinities which can include substantially any number of private affinities (referred to either individually or collectively as private affinities 108), each of which can describe or relate to user 106. Typically, private affinities 108 are cryptographically protected from public inspection, either by way of encryption, access or authorization control beyond what is necessary to access profile 104, or by some other means. In addition to private affinities 108, profile 104 can also include public affinities that are publicly accessible as well as other public or private data, which is further detailed in connection with FIG. 2A.

As used herein, an affinity can relate to a natural attraction or feeling of empathy or kinship (e.g. to a person or thing). Moreover, affinities can relate to one or more of likes, preferences, behaviors, activities, habits and so forth of an individual, which can be distinguished from settings or preferences, etc. associated with a device, service, or the like. While many conventional profiles, or conventional systems that include profiles, employ affinities to some degree, such is done in a public fashion. In other words, most conventional profiles (as opposed to profile 104) do not or cannot distinguish between public affinities (e.g., that are available to all who view the profile) and private affinities (e.g., that are only available to a subset of those who view the profile). While some systems do require membership with the host or authorization by a member (e.g., adding another as a friend or contact) before one can access the member's profile, once accomplished, substantially all affinities are publicly available. Thus, publicly available or accessible to public inspection are both generally intended to relate to a degree of authorization that is substantially the same level of authorization required to access the underlying profile (e.g. being a member of a service or being in a particular social network, social circle, or on a friend list).

Hence, most users of conventional profiles today understand that any affinity (or other information) included in an associated profile can be viewed by any third party who accesses that profile. This situation can substantially serve as a chilling effect on self expression or at least result in a profile that is a less accurate or less comprehensive representation of the associated user. For example, certain affinities especially those relating to fringe interests, eccentricities, or topics about which there is a common misconception or very little mainstream familiarity or understanding are generally omitted rather than included in conventional profiles, as these affinities might be a source of shame or embarrassment or incur undue explanation. Additionally, certain cautious or prudent users may forego detailing an affinity that is not politically correct or one that might easily be taken out of context by others or virtually any affinity that can be the source of the slightest bit of embarrassment or conflict with a desired image.

Appreciably, even though a user might hesitate to publish certain affinities publicly, such affinities can make for excellent engagement criteria, serve as conversation topics or to "break the ice," or even result in planning joint excursions or other shared experiences. Yet, while these affinities remain unknown, they cannot be utilized to match individuals. For example, suppose two users, Ashley and Ross, are both young professionals and both like a specific series of comic books. However, both parties understand that comic books are often viewed as fanciful or juvenile, and, as such, to indicate an interest in comic books in one's profile might lead to embarrassment or inappropriate characterizations. Accordingly, it is very likely that neither Ashley nor Ross will know of their common affinity, except by chance.

Furthermore, this unfortunate situation can arise even though Ashley and Ross are colleagues or otherwise familiar with one another, but have previously never broached the subject of comic books for the very same (or similar) reasons why they may not detail this information in a profile about themselves. It is further quite likely that, given the knowledge of the existence of a shared affinity for comic books, either or both Ashley or Ross might be willing to share certain information (e.g., the affinity or one's identity in connection with the affinity) with the other that would otherwise not be shared publicly or with other parties.

In accordance therewith, system 100 can further include matching component 110 that can compare one or more private affinities 108 from set $108_S$ to one or more disparate affinities 112 (from set $112_S$ of disparate affinities) included in disparate profile 114. Disparate profile 114 can be associated with disparate user 116 similar in manner to the relationship described between profile 104 and user 106. As depicted, both profile 104 and disparate profile 114 can be received by cryptography component 102, which can internally or privately resolve or expose private affinities included in either profile (e.g., profile 104 or disparate profile 114), which can include substantially any decryption-based technique or technology; or can additionally or alternatively relate to preparing or facilitating cryptographic comparisons of non-decrypted data, potentially in connection with matching component 110 (e.g., ciphertext comparisons or without accessing plain text data).

Matching component 110 can thus identify matching affinity 118 that correlates with private affinity 108. For example, disparate affinity 112 that correlates with private affinity 108 can, thus, be designated as matching affinity 118. It should be appreciated that disparate affinity 112 need not necessarily be private, even though private affinity 108 is. In fact, disparate affinity 112 can be a disparate public affinity (e.g., data about disparate user 116 that is freely accessible via disparate profile 114) or a disparate private affinity (e.g. data about disparate user 116 included in disparate profile 114 that is protected from public inspection). Thus, drawing again from the previously introduced example, suppose Ashley designates her affinity for comic books as private, whereas Ross does not mind if others learn this information about him and therefore makes his comic book affinity public. In this case Ashley might still be unaware of the shared affinity even though a close colleague of user Ross, e.g., because Ashley has never actually examined Ross's profile. Likewise, Ross will even more certainly be unaware of the shared affinity since Ashley's comic book affinity is protected and not freely disseminated or available.

However, regardless of the particulars, Ashley and Ross will most likely be interested in learning about that shared comic book affinity, which could potentially serve as the very engagement criterion that leads ultimately to a lasting or deeper friendship. In accordance therewith, system 100 can also include notification component 120 that can generate message 122 that can indicate matching affinity 118 has been identified. Hence, message 122 can relate information such as "We have discovered someone with a matching affinity," or message 122 might be more specific as to matching affinity 118, indicating "We have discovered someone else who likes comic books" and/or the same particular series of comic books described by private affinity 108. It should be appreciated that while Ashley might be quite interested in others who share her affinity for comic books, she may not want to be inundated with a large number of messages or may not want to receive message 122 when disparate user 116 is a random stranger or where no other historic or temporal relationship exists. Accordingly, rather than matching between all or a random subset of disparate users 116, matching component 110 can compare private affinity 108 to disparate affinity 112 when user 106 and disparate user 116 exchange a communication and/or have a history of communications. Likewise, matching component 110 can compare private affinity 108 to disparate affinity 112 when user 106 and disparate user 116 are in close geographic proximity. Hence, message 122 can relate only to those with established relationships with user 106 or, those in, say, the same room or location or setting (e.g., a conference, a nightclub . . . ) as user 106. Of course other examples can exist for meeting some suitable criterion before performing the matching or delivering message 122.

In addition, message 122 can also include various public data or other relevant information known or available at that time. For example, in the most recent scenario, the fact that Ross has an affinity for comic books is publicly displayed for any who can access his profile. Thus, assuming Ashley has such privileges, associated information can be included in message 122. Hence, Ashley can receive message 122 indicating, e.g., "Did you know that Ross is a fan of the same comic books as you?" However, Ross will generally not receive analogous information (unless authorized) given the fact that Ashley's affinity for comic books is private.

Naturally, user settings can be adjusted so that private affinities 108 are automatically revealed, but only to disparate users 116 with matching affinities 118. Thus, upon identification of matching affinity 118, one or both parties can be provided suitable information relating to the matching affinity 118 or the other party, even though such a setting will generally not be recommended. However, in the interest of additional privacy or to mitigate bait-and-switch practices and/or "trolling," "baiting," or "fishing," phenomena, further privacy measures can be implemented. For example, notification component 120 can facilitate or ensure that private information is only revealed with express authorization or at the express behest of user 106 (or similarly disparate user 116). Accordingly, notification component 120 can also provide request 124 relating to permission to publish to disparate user 116 certain revealed information included in profile 104, such as information relating to private affinity 108, an identity of user 106, a location of user 106 to name but a few examples. Revealed information is generally information that is private in some context, but is authorized to be shared, as is further detailed in connection with FIG. 2A.

Figure 2A:
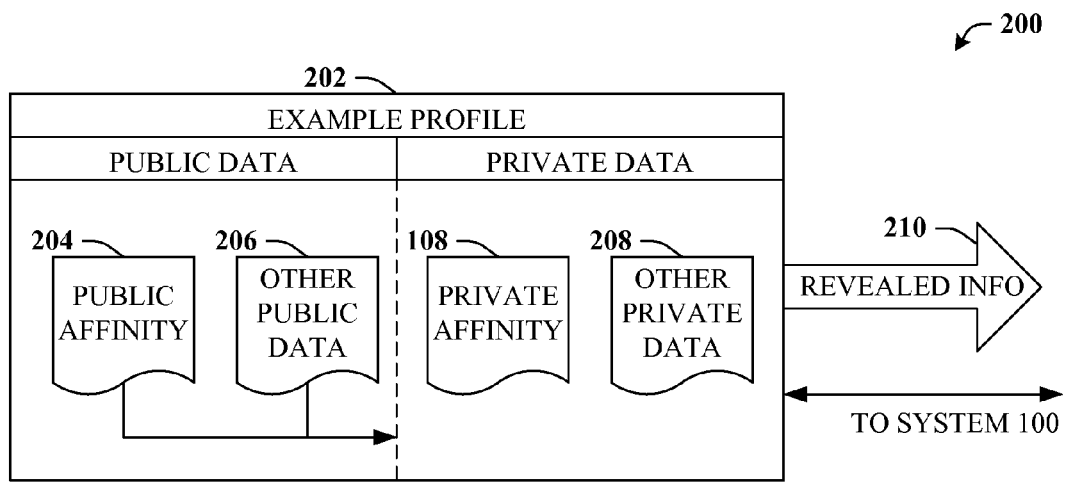
FIG. 2A is a graphical block diagram illustrating an example profile.

Turning now to FIG. 2A, a graphical illustration 200 of an example profile is provided. Example profile 202 is intended to reflect various features of either profile 104 or disparate profile 116 discussed supra in connection with FIG. 1. Profile 202 can include a variety data that can be characterized as either public data or private data. Public data can include one or more public affinities 204 as well as other public data 206 such as, e.g., certain descriptive or demographic information, etc. Typically, public data is accessible to public inspection and therefore can be scrutinized upon access to profile 202. In contrast, private data, such as private affinity 108 or other private data 208 is not (and potentially never is) accessible by merely inspecting profile 202. Other than private data that the user has entered, the other sources of private data can be from sources common to the users. For example, in an enterprise setting, the private data may consist of previous projects that an user worked on, the cities that the user has worked in, etc.

As previously discussed, notification component 120 can transmit request 124 to publish revealed information 210, which can be information from profile 202, usually information that is classified as private data. Likewise, message 122 can include substantially any public information. However, notions or classification of public versus private can change based upon context. In particular, in the context of browsing profile 202, what is deemed public affinities 204 and other public data 206 are classified here as public data. However, in the context of revealed information 210 (e.g., information that is provided to a disparate party), all or portions of public data can be migrated or reclassified as private data.

To illustrate this distinction, recall the previous example in which Ashley designates her comic book affinity as a private affinity, yet Ross publicly discloses his comic book affinity. Thus, Ashley's affinity can be exemplified by private affinity 108 included in the private data section, whereas Ross's affinity can be exemplified by public affinity 204 included in the public data section. It is readily apparent that in the context of sharing relevant information (e.g., by way of revealed information 210), Ashley would generally need to expressly authorize any publication to Ross that they share an affinity for comic books. On the other hand, Ross need not necessarily provide express authorize for this information to be published to Ashley, since Ashley could freely obtain the information and the associated relationships between the two sets of information by examining Ross's profile.

However, simply because information publicly exists in profile 202 that can be reviewed upon normal inspection, notification component 120 or other components detailed herein do not necessarily treat that data as public in all cases. For example, as we have already seen, without authorize from Ashley, Ross will not be apprised of the fact that Ashley likes the same comic books he does, since this is a private affinity 108 in Ashley's profile. Yet, Ashley's profile may include public information (e.g., other public data 206) such as the following description: "Hi, my name is Ashley, and I live at 1234 Mockingbird Lane . . . ." While this information is indeed public and freely accessible to Ross should he visit Ashley's profile, it will not necessarily be treated as such in connection revealed information 210. In particular, strict protocols can be maintain to ensure that private affinities 108 (or any private data) are not inadvertently or indirectly revealed or discovered through statistical probing or correlations or the like. For example, all or portions of data included in a profile can be migrated to private designation or upgraded to a higher level of privacy that is equal to that which can potentially be revealed or is related in some manner to matching affinity 118.

Hence, while Ross can readily see Ashley's name and address when actively browsing her profile, he will not necessarily be privy to those facts in connection with the user who also likes comic books (or that public portions of profile 202 are associated with matching affinity 118) unless Ashley allows it. In other words, even though Ross might easily learn Ashley's address, he will not know that that address (even though public) relates to the person who shares an affinity. Conversely, since all information associated with Ross in connection with matching affinity 118 is already public, potentially any other public information available from profile 202 can be actively transmitted to Ashley. Additional features associated with transmitting revealed information 210, or other communications, can be found in connection with FIG. 4, infra.

Figure 2B:
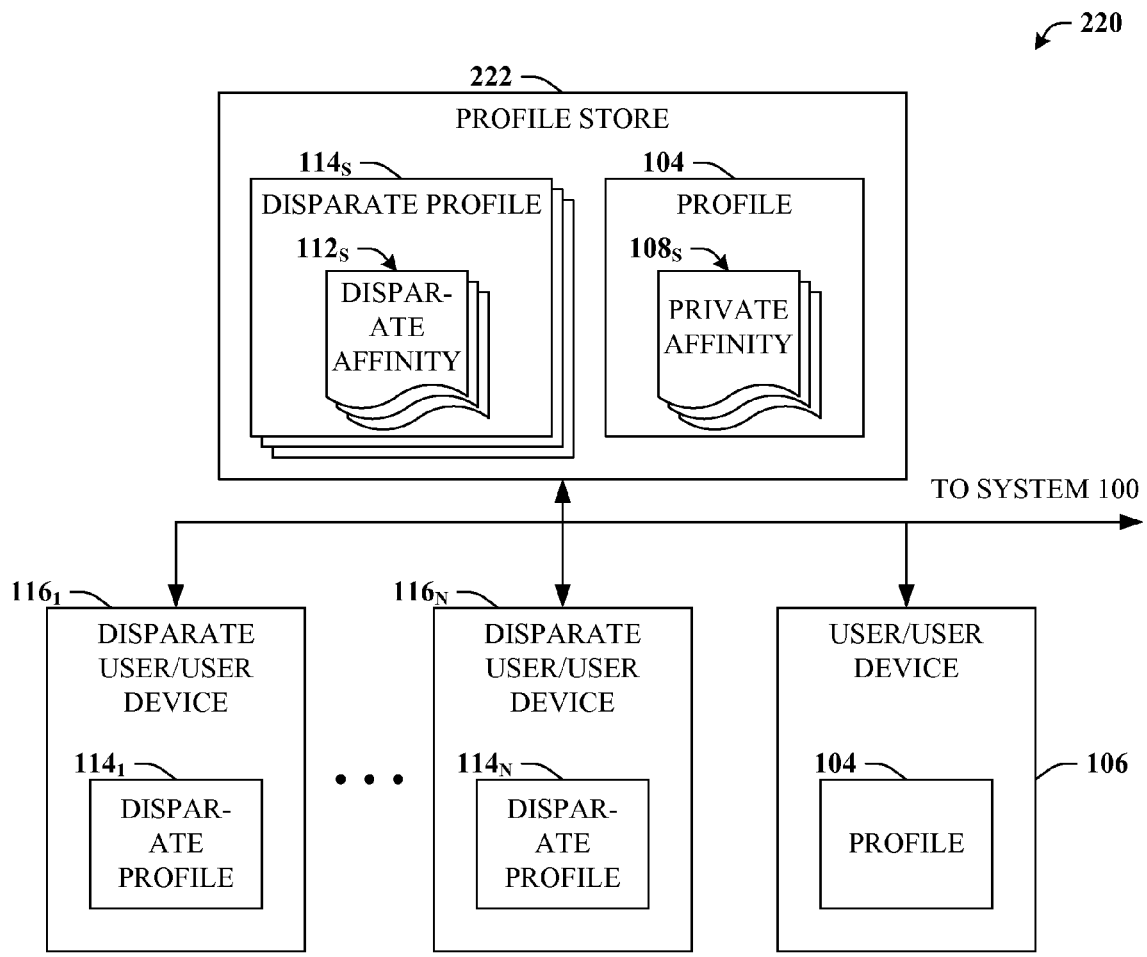
FIG. 2B depicts a graphical block diagram that illustrates various topologies relating to storing and/or accessing information included in the profile.

Referring now to FIG. 2B, graphical diagram 220 depicts various topologies relating to storing and/or accessing information included in the profile. As a first example, all profiles, including profile 104 and substantially any number of disparate profiles included in set $114_S$ of disparate profiles can be contained in profile store 222. Appreciably, profile 104 can include at least set $108_S$ of private affinities and each disparate profile 114 can include at least set $112s$ of disparate affinities. It should also be appreciated that profile store 222 can be included in or operatively or communicatively coupled to system 100.

Profile store 222 can aggregate disparate profiles 114 from substantially any number, N, of disparate users (or disparate user devices, which can be a proxy for disparate user 116), labeled here as $116_1$-$116_N$, while obtaining profile 104 from user 106 and/or an associated device. In another aspect, a central storage mechanism such as profile store 222 is not necessary such that all profiles are distributed only on, and are accessed by way of, communication with the individual devices/users (e.g., 106 and $116_1$-$116_N$).

Figure 3:
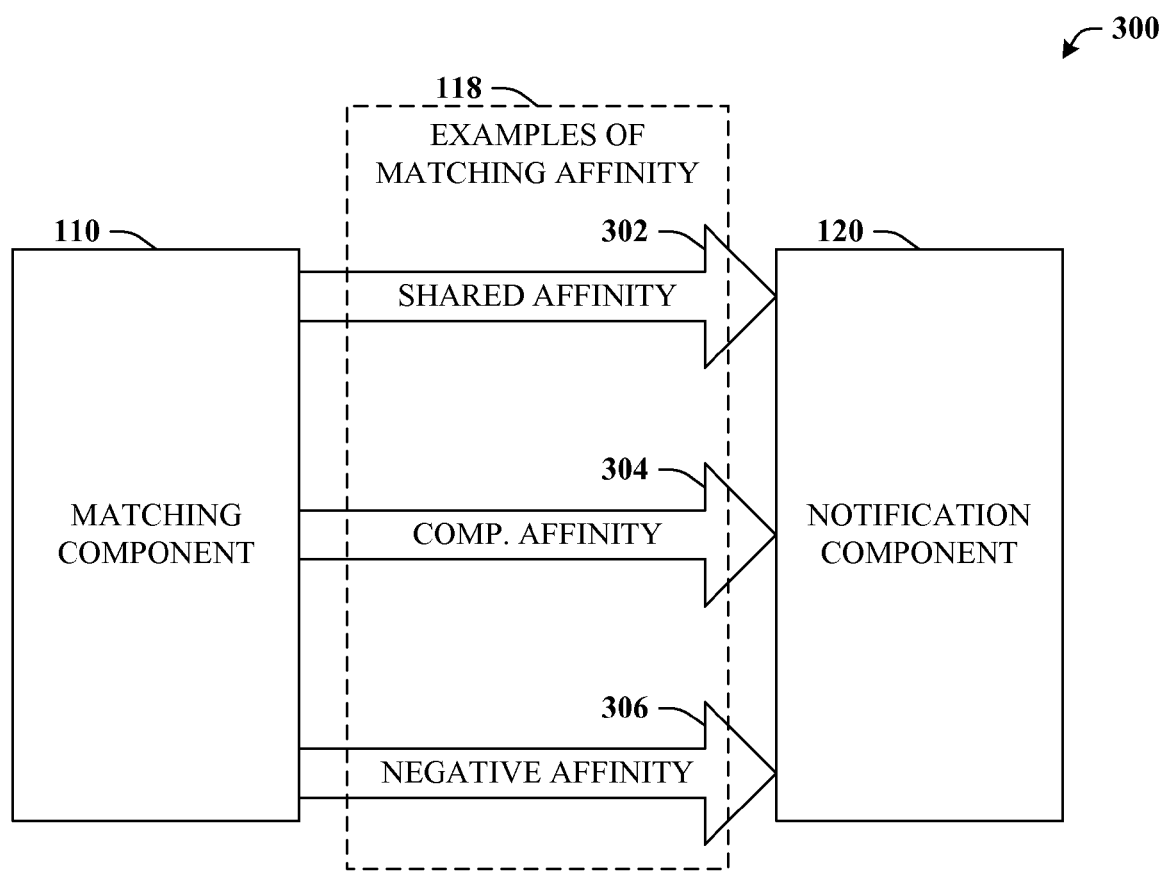
FIG. 3 provides a block diagram of a system that can identify various kinds of matching affinities.

With reference now to FIG. 3, system 300 that can identify various kinds of matching affinities is illustrated. As indicated supra, matching component 110 can compare private affinity 108 to disparate affinity 112 in order to identify matching affinity 118, wherein matching affinity 118 correlates with private affinity 108. Matching component 110 can then propagate matching affinity 118 to notification component 120. In one or more aspects, matching component 110 can identify matching affinity 118 when disparate affinity 112 is substantially identical to private affinity 108, which can be denoted shared affinity 302. The previously described examples in which Ashley and Ross both share an affinity for a particular series of comic books are an example of shared affinity 302, since both parties share an identical or a substantially similar affinity.

However, other types of correlations and/or types of matching affinities 118 are contemplated to exist. For instance, matching component 110 can identify matching affinity 118 when disparate affinity 112 substantially complements private affinity 108, as illustrated by complementary affinity 304. Broadly speaking, in this case, rather than identifying disparate user 116 who is like user 106 (in terms of an affinity), matching component 110 can identify a disparate user 116 who complements user 106. Complementary affinities 304 can be employed in connection with substantially any scenario in which certain types of dynamics exist such as those relating to producer-consumer dynamics, client-server dynamics, or team-specialization dynamics (e.g., for dating or competitive applications). As one basic illustration, consider a first user who likes to drive, while a second user needs a ride to a particular destination. These or other scenarios can readily provide a basis for complementary affinities 304.

In another case, negative affinity 306 can exist, such as when matching component 110 identifies matching affinity 118 when disparate affinity 112 substantially conflicts or clashes with private affinity 108. For example, consider the case in which Ashley enjoys shopping, but not in the presence of teen-age girls who tend to travel in groups and always seem to be loud and obnoxious in Ashley's opinion. Hence, there exists the potential to detect negative affinities 306, such as when Ashley desires to buy more of her favorite foundation, but the makeup-counter is currently occupied by teenagers. Appreciably, in this example, an object for Ashley is to avoid one or more disparate users 116 rather than to meet or contact the disparate user 116. Hence, rather than engage in contact or negotiations (detailed further in connection with FIG. 4), matching component 110 can focus on disparate affinities 112 that are public, rather than private ones that typically require authorization before revealing.

Figure 4:
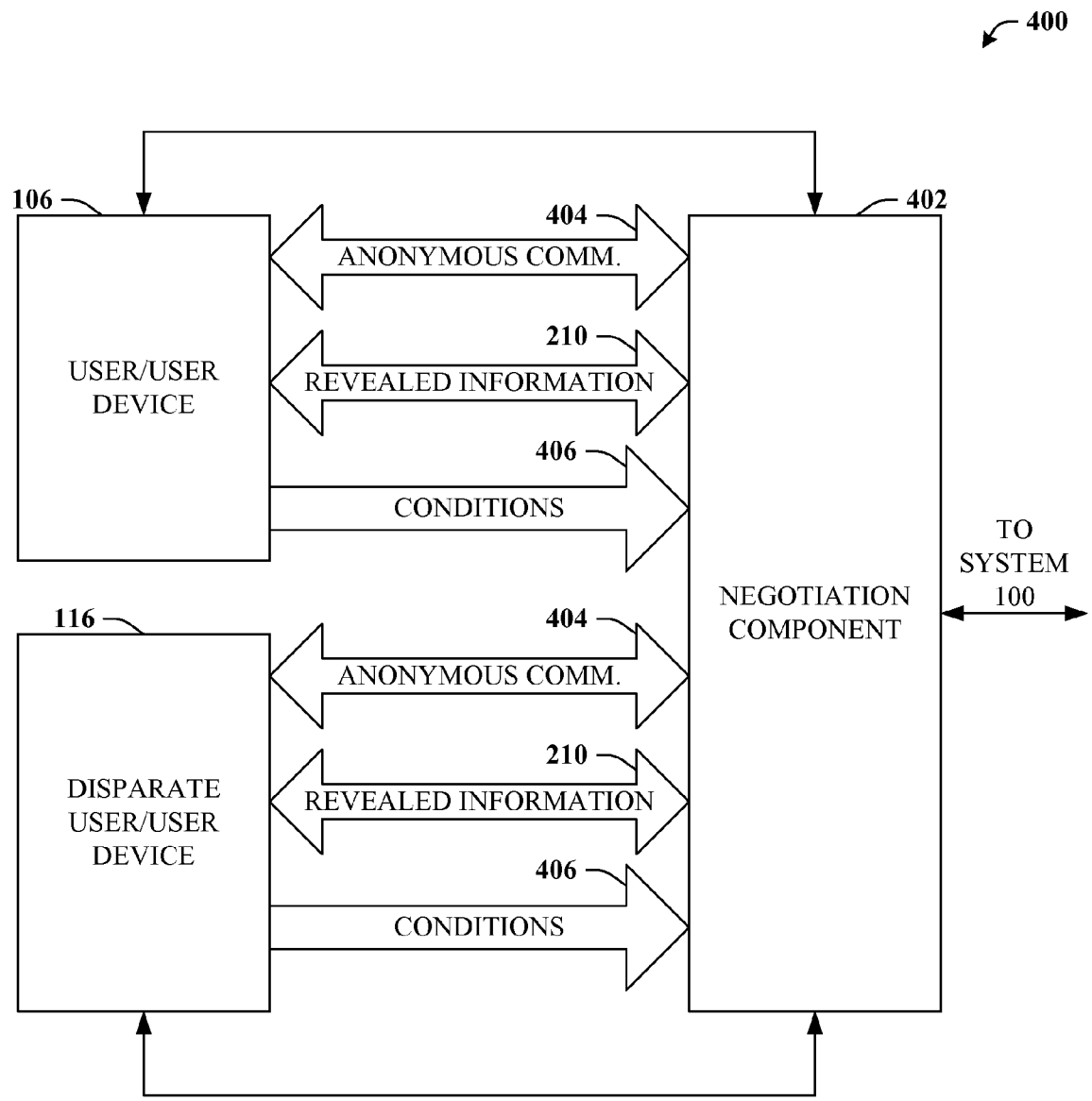
FIG. 4 illustrates a block diagram of a system that can mediate between a user and a disparate user in order to facilitate or enrich a personal relationship.

Turning now to FIG. 4, system 400 that can mediate between a user and a disparate user in order to facilitate or enrich a relationship is depicted. In particular, system 400 can include negotiation component 402 that can broker an exchange between user 106 and disparate user 116. For instance negotiation component 402 can facilitate anonymous communication 404 between user 106 and disparate user 116. To illustrate, we return again to the familiar example in which Ashley and Ross both maintain a private affinity for comic books introduced in connection with FIG. 1. Once matching component 110 identifies the matching affinity 118, notification component 120 can provide Ashley message 122 indicating, e.g. "We've located someone who shares your affinity for comic books. The two of you might have a lot in common."

At this point, while Ashley does not know who the other party is (Ross), she can still communicate with that other party by way of negotiation component 402. For example, Ashley can compose a message stating, e.g., "Hi, we both like the same series of comic books. It would be nice to learn more about you. Are you up for exchanging more info?" Ashley's message can thus be transmitted to negotiation component 402 as anonymous communication 404. Negotiation component 402 can then forward the message to Ross. Hence, Ashley can deliver a message to Ross even though she does not know to whom the message is directed, while Ross can receive the message from Ashley even though he does not know the origin of the message. Naturally, Ross can reply anonymously in a similar way.

In one or more aspects, negotiation component 402 can propagate revealed information 210 to or from user 106 or disparate user 116. As discussed supra, revealed information 210 can be expressly authorized for sharing. For example, continuing the above example, notification component 120 can transmit request 124 to Ashley inquiring, e.g., whether it is acceptable to publish revealed information 210 to Ross. More specifically, revealed information 210 can relate to an identity of user 106, a location of user 106, private affinity 108 to name but a few examples of revealed information 210. For instance, revealed information 210 can inform Ross that matching affinity 118 (e.g. the shared affinity for comic books) relates to an individual identified as Ashley. Additionally or alternatively, revealed information 210 can inform Ross that some individual (potentially anonymous at this point) near Ross's current locale shares the affinity. Likewise, revealed information 210 can particularly identify matching affinity 118. An example of this can be when message 122 indicates "Someone in this room shares one of your affinities." Thus, the location is known (or previously revealed by one or more parties), yet which particular affinity is shared is not (yet) known and can thus be revealed.

In fact, determining whether or not to reveal certain information as well as when and how information is revealed can be expansively and flexibly managed or facilitated by negotiation component 402. In particular, negotiation component 402 can propagate revealed information 210 only after certain conditions 406 are satisfied. These conditions 406 can relate to or include a mutual exchange of revealed information 210, an assurance or existence of k-anonymity, or the like. In more detail, conditions 406 that relate to a mutual exchange can provide that revealed information 210 is transmitted to negotiation component 402, where upon such data can remain private or undisclosed unless or until satisfactory information is received from another party. Only after both parties have provided or authorized publication of the satisfactory information will that information be revealed. Conditions 406 that relate to k-anonymity can require that information is only revealed if there is a statistical threshold guarantee of anonymity based upon some value, k. For instance, unless there are at least k−1, possibilities applicable to the revealed data 210, such data will not be published.

To provide a few concrete illustrations of the above, consider once more the scenario in which Ashley and Ross both share a private affinity for comic books. Suppose further that both Ashley and Ross are attending the same lecture relating to endangered species, and it is known that at least 75 people are presently in attendance in the lecture room. In this case, Ashley can receive message 122 stating, e.g., "We've identified an individual with a shared affinity whom you may be interested in getting to know." Furthermore, notification component 120 can provide request 124 inquiring whether it is acceptable to reveal certain location information to this individual (Ross). Ashley responds to request 124 in the affirmative. Suppose further that Ross responds in the affirmative to a similar request 124 to him or that Ross previously set a default to automatically reveal, say, certain location information on the condition that the other party provides the same data or some other acceptable data (e.g. condition 406 based upon mutual exchange). Hence, negotiation component 402 is appraised of the fact that both Ashley and Ross are attending the lecture, and that both are willing to reveal certain location information. Hence, revealed data 210 can substantially inform Ashley or Ross that, e.g., "Someone at this lecture has a matching affinity with you."

Rather than based solely upon a mutual exchange, suppose Ashley indicates (or sets a default) that revealed information 210 can only be shared when there is some guarantee of anonymity. For example, Ashley can indicate that she will only reveal the above-mentioned location if there are at least 20 other people. Since there are at least 75 individuals at this lecture, the same message can be delivered to Ashley that "Someone at this lecture has a matching affinity with you," but appreciably, negotiation component 402 in this case checked not only that Ross met the condition 406 of mutual exchange (e.g., authorizing that his location information is shared), but that k-anonymity was also met.

Next suppose Ashley receives anonymous communication 404 from Ross (while still uncertain of the identity of Ross) stating, "Hey, I noticed you and I share an affinity and we are both at the endangered species lecture. I'll give you my ID if you give me yours, quid pro quo." Ashley is interested by this proposition, but decides to add a layer of intrigue. For example, Ashley decides it would be much more fun if the two get together without knowing which affinity they share. That way, the couple can engage in light conversation during the forthcoming intermission, attempting to probe one another to figure out specific things they have in common or the like. In this case, Ashley can again rely upon k-anonymity by, e.g., agreeing to reveal her identity to Ross, but only if Ross (and potentially Ashley herself) have at least, say, 15 (or another k-based value) private affinities in their respective profiles, any one of which could be the actual matching affinity 118.

Figure 5:
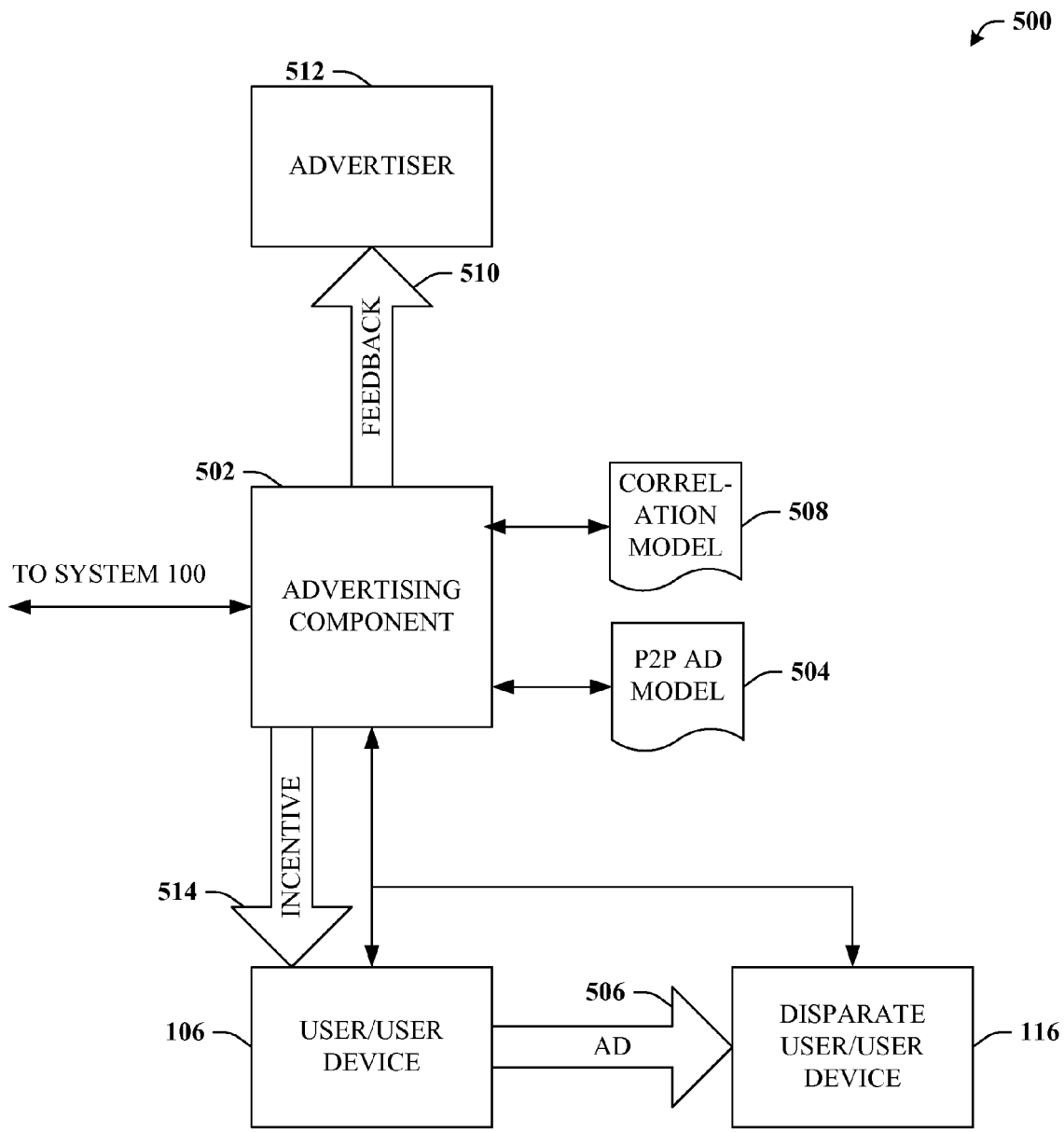
FIG. 5 depicts a block diagram of a system that can employ various ad-based models in order to leverage advertising opportunities in connection with affinities or relationships related thereto.

With reference now to FIG. 5, system 500 that can employ various ad-based models in order to leverage advertising opportunities in connection with affinities or relationships related thereto is provided. Generally, system 500 can include advertising component 502 that can be included in or operatively coupled to system 100. Advertising component 502 can employ peer-to-peer (P2P) ad model 504 that can facilitate delivery of advertisement 506 disparate user 116 by way of user device 106, or vice versa. It should be appreciated that P2P transfers of advertisements 506 can be much more convenient from a networking perspective, given that conventional methods that transfer advertisements from the advertiser to the ad target must first have contact information, which tends to be very difficult for advertisers to obtain. Moreover, P2P transfers provide an additional benefit to advertisers since the ad target is much more likely to devote attention to an ad received from a known individual as opposed to, e.g., an unsolicited ad from an advertiser.

For instance, an ad from a friend or from someone with whom user 106 has matching affinity 118, especially in the case where the ad relates to matching affinity 118 (e.g. an ad for the latest edition of a comic book series), will generally carry more weight and/or demand more attention from the receiver of the advertisement. Thus, supposing Ashley and Ross are introduced or reconnected due to a shared affinity for comic books, Ross might be particularly interested in information relating to Ashley's most recent purchase. Such information can be delivered to Ross directly from Ashley's device, which can potentially include a stored history of the purchase. P2P ads can thus be much more effective, and therefore command a premium in terms of pay-per-impression, per sale, etc.

According to one or more aspects, advertising component 502 can also employ correlation model 508 in order to provide feedback 510 to advertiser 512. It should be appreciated that feedback 510 is generally intended to be anonymous data, often of a statistical nature, and therefore common privacy concerns will not typically arise. Regardless, feedback 510 can still require express authorization before data associated with user 106 can be employed, or be based upon an explicit opt-in condition. To provide an example of feedback 510 based upon correlation model 508, consider once more the above example in which Ashley attends the lecture on endangered species in which it is known that at least 75 participants (e.g., Ashley and 74 disparate users 116 of the disclosed subject matter) are in attendance. Feedback 510 need not relate to the fact that Ashley or any of the others attended this lecture or anything that is specifically applicable to personal information. Rather, suppose that a significant percentage of the known attendees, say, above what would be expected from a random sample, have an affinity for red wine.

In that case, advertiser 512 that is a producer or retailer of red wine will likely be very interested in such information. Therefore, even though in this case advertiser 512 is not provided information relating to a particular user's affinity for red wine or that a particular user attended the endangered species lecture, that advertiser 512 can discover potentially new or especially receptive markets for its products or for ad targeting by way of feedback 510. It should be appreciated that advertisement 506 and/or feedback 510 can relate to private affinity 108. It should also be appreciated that incentive 514 can be provided to user 106. For example, in exchange for delivering advertisement 506 to disparate user 116, user 106 can be provided a credit, coupon, or revenue share. Likewise, similar incentives can be provided to user 106 (or others) in exchange for providing or authorizing feedback 510. It should further be appreciated that feedback 510 can also incorporate actual input or behavior from the recipient of an ad. For example, when the recipient actually perform action related to the ad such as, e.g., clicking on an embedded URL or delete without viewing.

Figure 6:
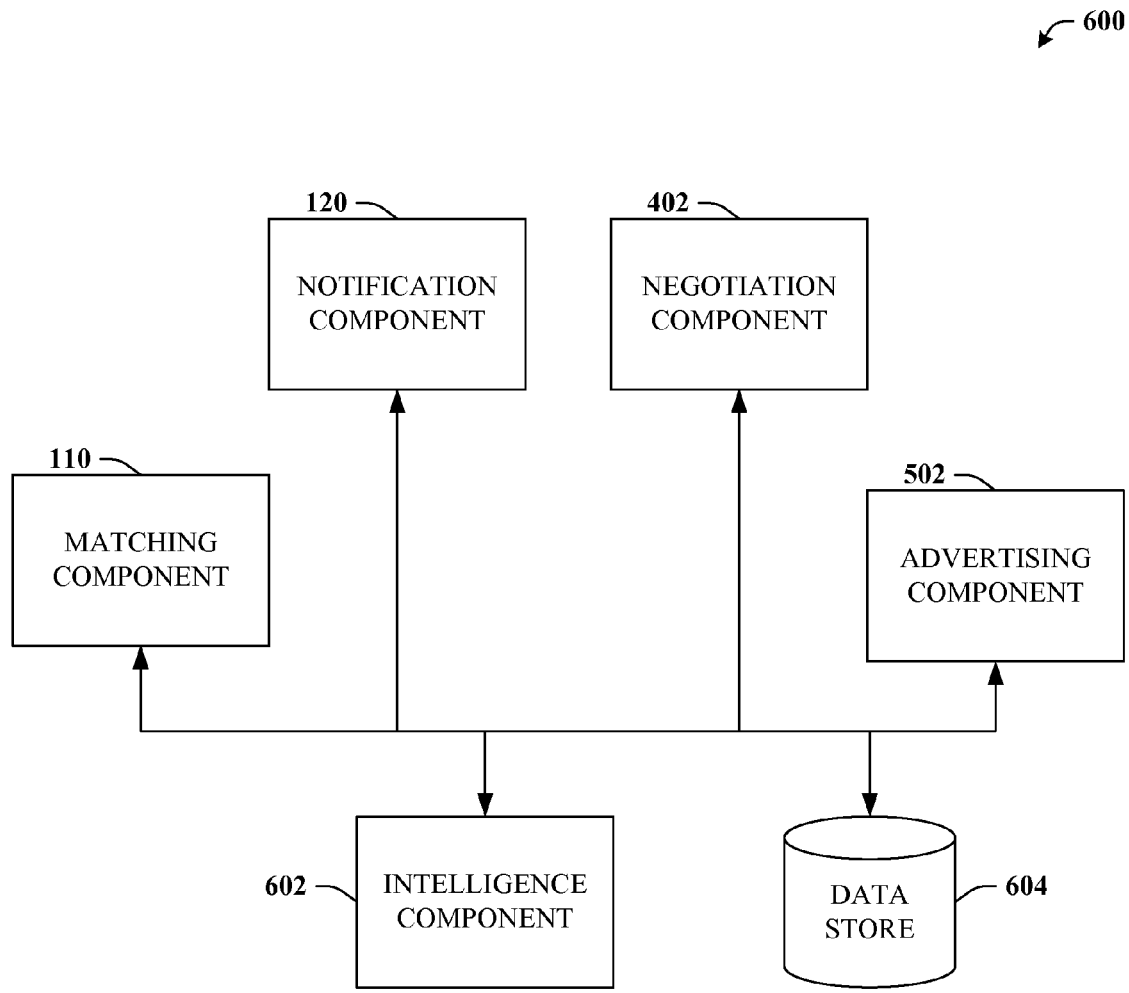
FIG. 6 is a block diagram of a computer-implemented system that can perform or aid with various determinations or inferences.

Now turning to FIG. 6, system 600 that can perform or aid with various determinations or inferences is illustrated. Generally, system 600 can include matching component 110, notification component 120, negotiation component 402, and advertising component 502 as substantially described herein. In addition to what has been described, the above-mentioned components can make intelligent determinations or inferences. For example, matching component 110 can identify matching affinity 118, which can include identical affinities, but can also include substantially similar affinities, complementary affinities, or in some cases even negative affinities. Thus, determining matching affinity 118 can rely upon, e.g., Bayesian probabilities or confidence measures or based upon machine learning techniques related to historical analysis, feedback, and/or other determinations or inferences.

Likewise, notification component 120 can employ similar techniques in order to learn or tailor suitable messages 122 or requests 124 that are delivered to user 106. In a similar manner, advertising component 502 can utilize intelligent determinations or inferences to opportunistically customize or tailor advertisement 506 based upon, e.g., the type of content included in advertisement 506 and/or the timing of delivery. In addition, advertising component 502 can intelligently determine or infer correlations that might be of interest to advertiser 512. Negotiation component 402 can also utilize intelligent determinations or inferences, e.g. to detect potential "affinity baiting," certain types of spam, or even potential fraud.

In addition, system 600 can also include intelligence component 602 that can provide for or aid in various inferences or determinations. In particular, in accordance with or in addition to what has been described supra with respect to intelligent determination or inferences provided by various components described herein. For example, all or portions of matching component 110, notification component 120, negotiation component 402, or advertising component 502 can be operatively coupled to intelligence component 602. Additionally or alternatively, all or portions of intelligence component 602 can be included in one or more components described herein. Moreover, intelligence component 602 will typically have access to all or portions of data sets described herein, such as data store 604. Data store 604 is intended to be a repository of all or portions of data, data sets, or information described herein or otherwise suitable for use with the claimed subject matter, and can potentially include other information stores or sources, such as profile store 222 of FIG. 2B or an advertisement store (not shown). Data store 604 can be centralized, either remotely or locally cached, or distributed, potentially across multiple devices and/or schemas. Furthermore, data store 604 can be embodied as substantially any type of memory, including but not limited to volatile or non-volatile, sequential access, structured access, or random access and so on. It should be understood that all or portions of data store 604 can be included in system 100, or can reside in part or entirely remotely from system 100.

Accordingly, in order to provide for or aid in the numerous inferences described herein, intelligence component 602 can examine the entirety or a subset of the data available and can provide for reasoning about or infer states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g. support vector machines, neural networks, expert systems, Bayesian belief networks, fuzzy logic, data fusion engines . . . ) can be employed in connection with performing automatic and/or inferred action in connection with the claimed subject matter.

A classifier can be a function that maps an input attribute vector, x=(x1, x2, x3, x4, xn), to a confidence that the input belongs to a class, that is, f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g. naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

Figure 7:
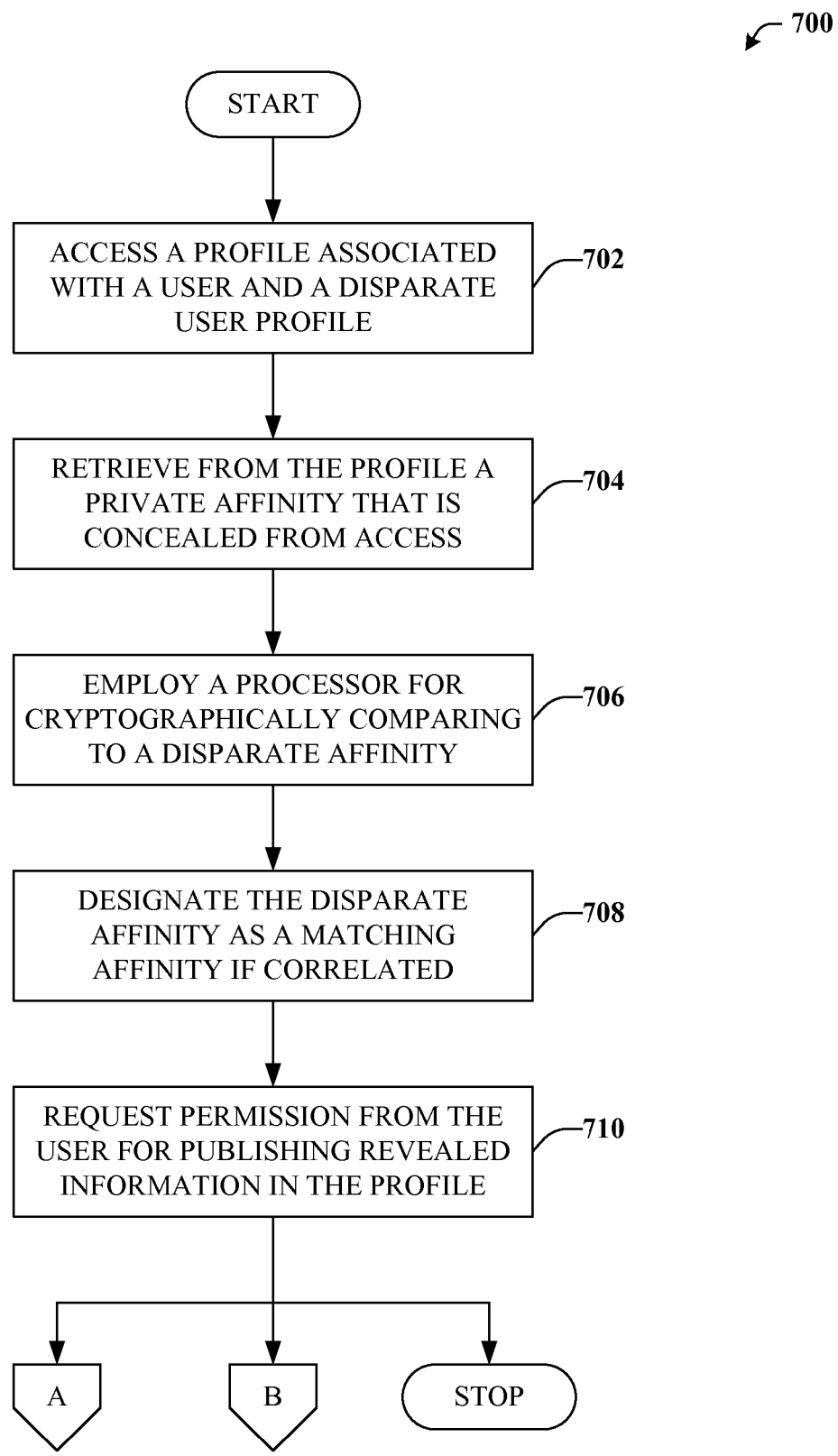
FIG. 7 depicts an exemplary flow chart of procedures that define a method for utilizing hidden affinities for establishing or enhancing personal relationships.
Figure 8:
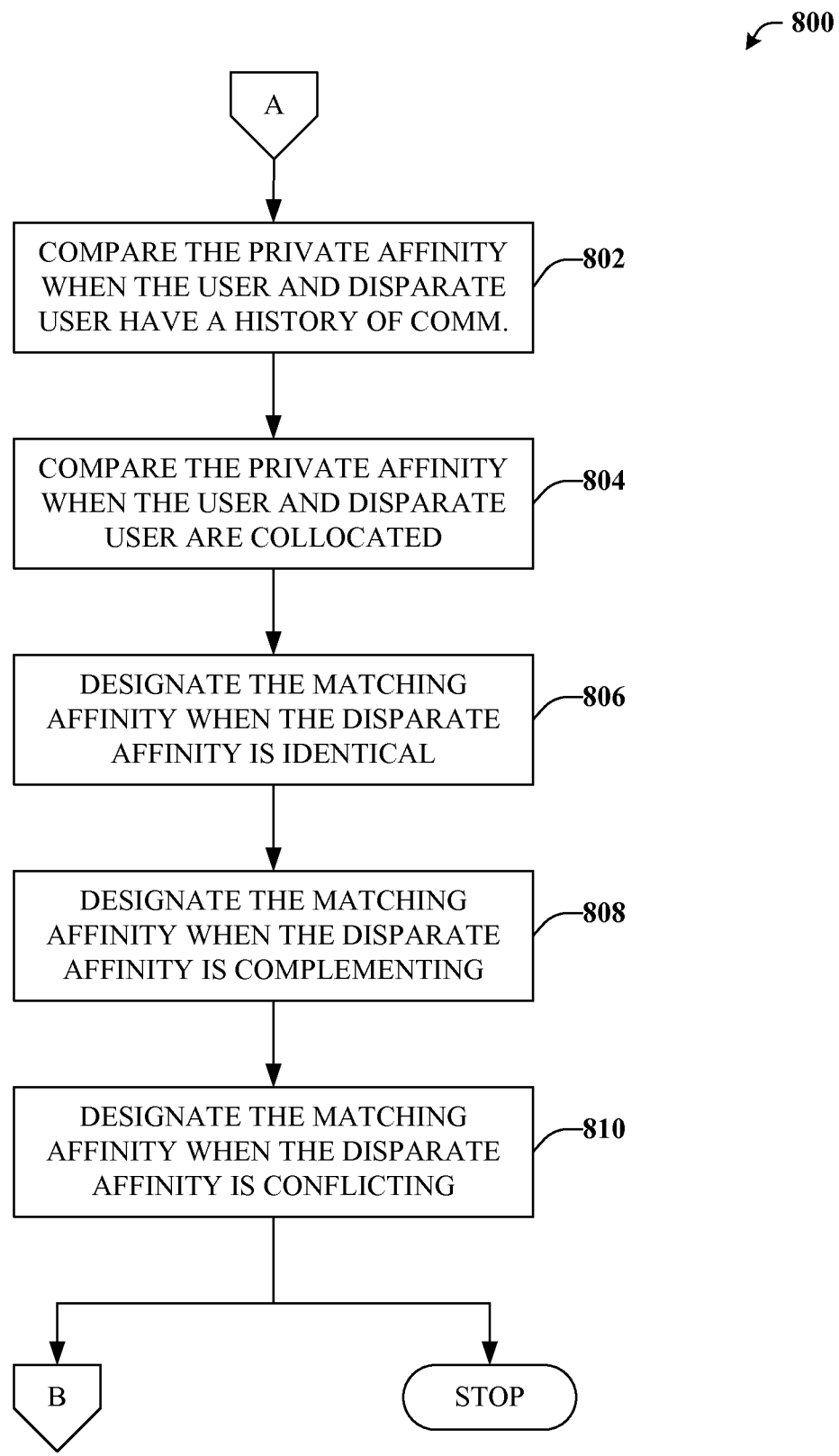
FIG. 8 illustrates an exemplary flow chart of procedures that define a method for providing additional features in connection with comparing affinities and/or designating matches.
Figure 9:
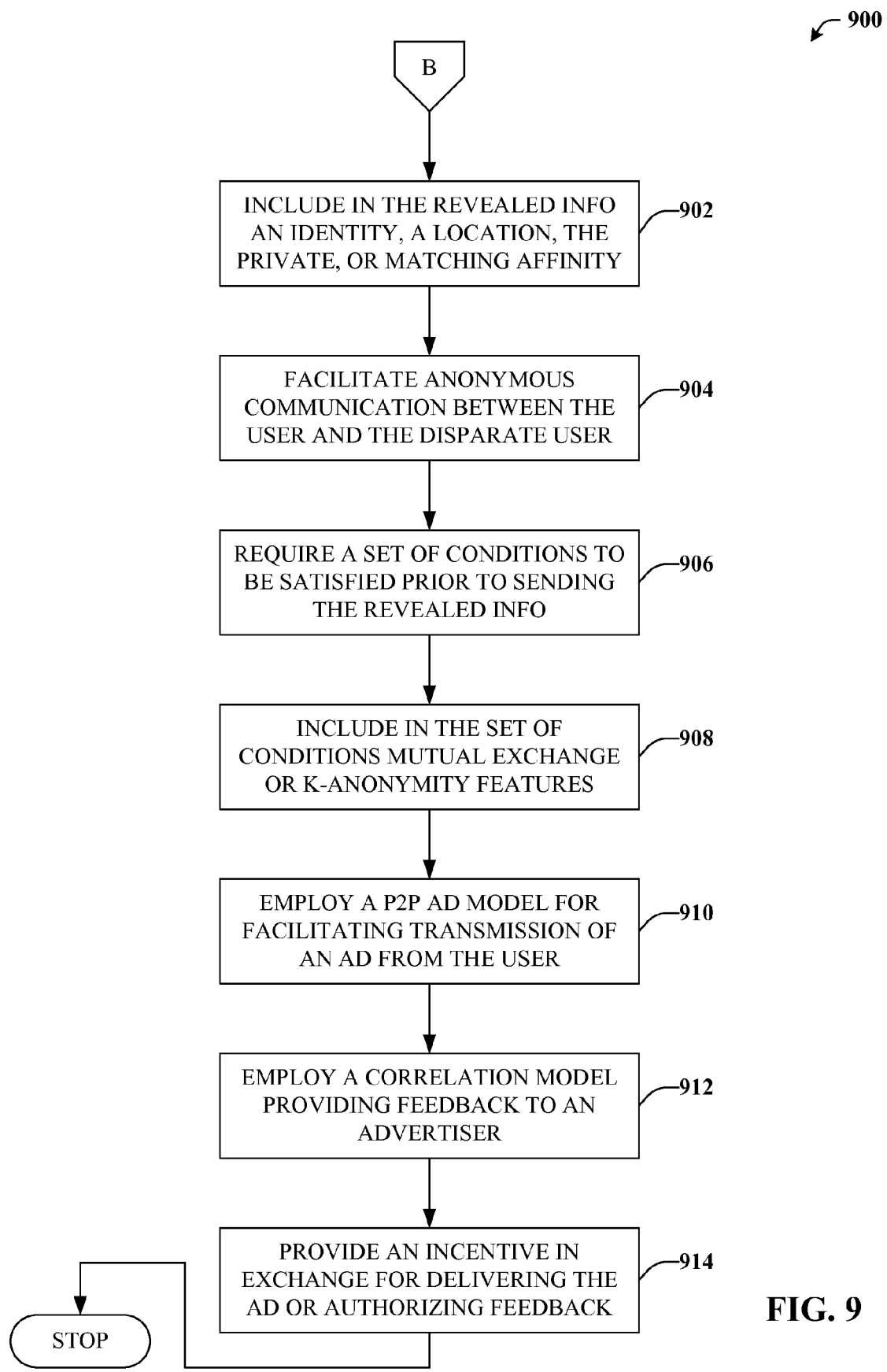
FIG. 9 is an exemplary flow chart of procedures defining a method for providing additional features in connection with leveraging affinities.

FIGS. 7, 8, and 9 illustrate various methodologies in accordance with the claimed subject matter. While, for purposes of simplicity of explanation, the methodologies are shown and described as a series of acts, it is to be understood and appreciated that the claimed subject matter is not limited by the order of acts, as some acts may occur in different orders and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the claimed subject matter. Additionally, it should be further appreciated that the methodologies disclosed hereinafter and throughout this specification are capable of being stored on an article of manufacture to facilitate transporting and transferring such methodologies to computers. The term article of manufacture, as used herein, is intended to encompass a computer program accessible from any computer-readable device, carrier, or media.

With reference now to FIG. 7, exemplary computer implemented method 700 for utilizing hidden affinities for establishing or enhancing personal relationships is illustrated. In general, at reference numeral 702, a profile associated with a user and a profile associated with a disparate user can be accessed. Both profiles will typically include affinities that describe, e.g., likes or interests of the associated user. In particular, one or more of these affinities can be private affinities that are protected from public access. In other words, the private affinities can be concealed from third-party inspection.

At reference numeral 704, a private affinity, potentially from a set of private affinities relating to the user, can be retrieved from the profile. At reference numeral 706, a processor can be employed for cryptographically comparing the private affinity to a disparate affinity that is included in the disparate profile.

Next to be described, at reference numeral 708, the disparate affinity can be designated as a matching affinity when the disparate affinity correlates with the private affinity in some manner. Hence, it can be determined when an affinity of the disparate user correlates with that of the user, and this correlating affinity can be designated as such. At reference numeral 710, permission from the user can be requested. In particular, permission for publishing to the disparate user certain revealed information that can relate to substantially any information that is included in the profile, but will typically be information that is considered, at least in some context, to be private Referring to FIG. 8, exemplary computer implemented method 800 for providing additional features in connection with comparing affinities and/or designating matches is depicted. At reference numeral 802, as described in connection reference numeral 706 of FIG. 7, the private affinity can be compared to the disparate affinity when the user and the disparate user establish a history of communication. Thus, discovering matching affinities between users can substantially apply only to users who have some connection or point of contact rather than to, say, random parties or complete strangers. Additionally or alternatively, at reference numeral 804, the private affinity can be compared to the disparate affinity when the user and the disparate user are substantially physically collocated. Appreciably, collation can often better facilitate face-to-face exploration and sharing and, moreover, can provide a suitable context or relationship even if there is no previous association or contact between the user and the disparate user.

At reference numeral 806, the matching affinity designated at reference numeral 708 can be identified when the disparate affinity is identical or substantially similar to the private affinity. Thus, the matching affinity can identified when two users share a common affinity. Appreciably, however, the correlation between affinities can be complementary as well. For instance, at reference numeral 808 the matching affinity can be designated when the disparate affinity substantially complements the private affinity. In contrast, at reference numeral 810, the matching affinity can be designated when the disparate affinity substantially clashes with the private affinity.

With reference now to FIG. 9, method 900 for providing additional features in connection with leveraging affinities is illustrated. For instance, at reference numeral 902, the revealed information discussed at reference numeral 710 can include, e.g., an identity of the user, a location of the user, an affinity of the user and so forth. At reference numeral 904, anonymous communication between the user and the disparate user can be facilitated. For example, communications can be transmitted to an intermediary before being anonymously forwarded to the anonymous recipient.

At reference numeral 906, a set of conditions can be required to be satisfied prior to transmitting the revealed information. In accordance with reference numeral 908, the set of conditions can include at least one of a condition of mutual exchange of revealed information or a condition associated with k-anonymity. Hence, information a user is willing to reveal to another can be transmitted to the intermediary, yet not actually published to the disparate party unless or until the disparate party herself provides the required revealed information or can meet certain guarantees associated with anonymity.

Figure 10:
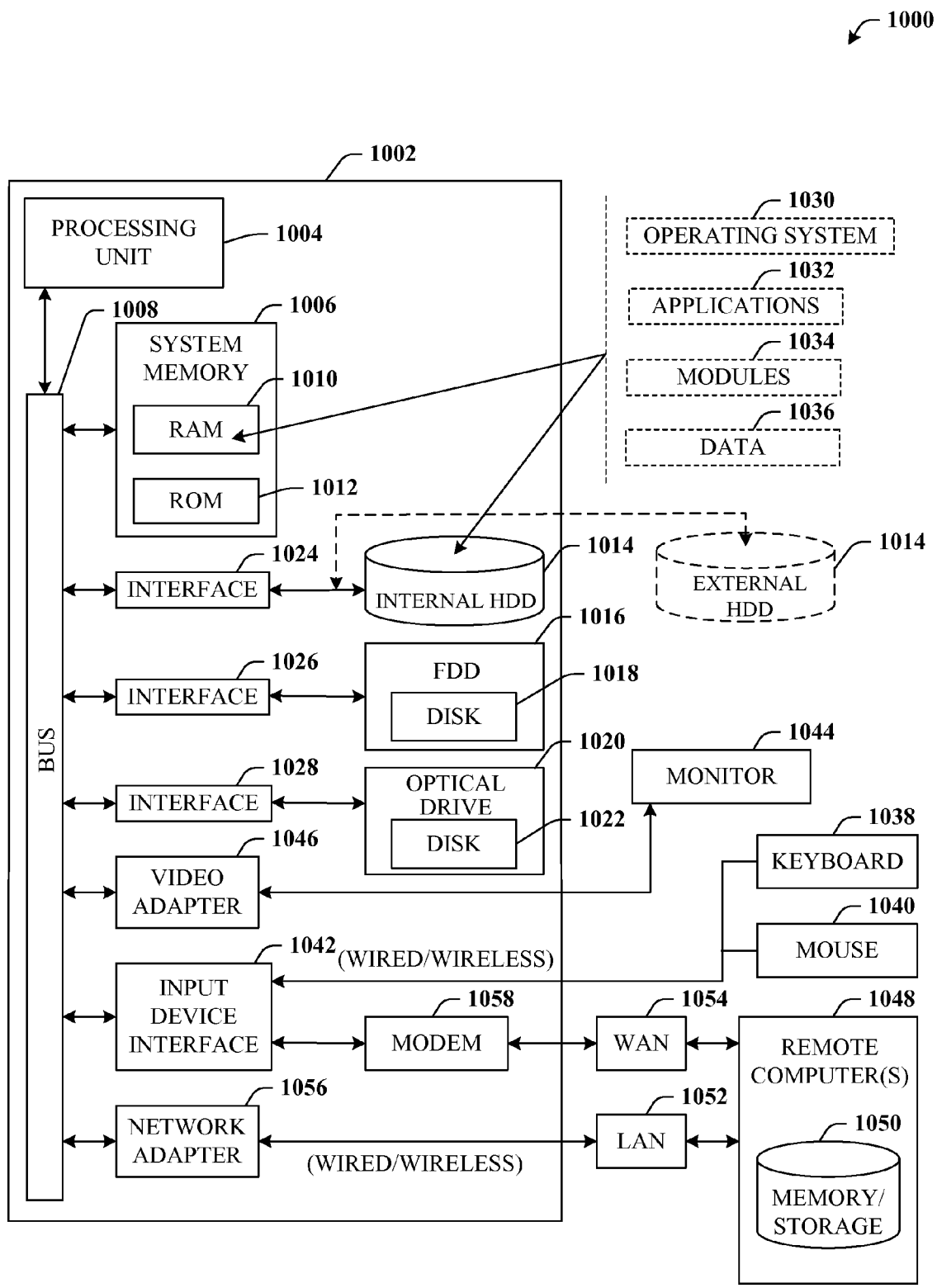
FIG. 10 illustrates a block diagram of a computer operable to execute the disclosed architecture.

At reference numeral 910, a P2P ad model can be employed for facilitating transmission of an advertisement from the user to the disparate user. Appreciably, the ad can, but need not, specifically relate to the matching affinity or another affinity associated with the user or disparate user. At reference numeral 912, a correlation model can be employed for providing feedback to an advertiser. The feedback can be substantially anonymous and relate to statistical correlations, generally in connection with an affinity. At reference numeral 914, an incentive can be provided to the user in exchange for delivering the advertisement to the disparate user. Additionally or alternatively, the incentive can be provided to the user (or disparate user) in exchange for authorizing feedback to the advertiser Referring now to FIG. 10, there is illustrated a block diagram of an exemplary computer system operable to execute the disclosed architecture. In order to provide additional context for various aspects of the claimed subject matter, FIG. 10 and the following discussion are intended to provide a brief, general description of a suitable computing environment 1000 in which the various aspects of the claimed subject matter can be implemented. Additionally, while the claimed subject matter described above may be suitable for application in the general context of computer-executable instructions that may run on one or more computers, those skilled in the art will recognize that the claimed subject matter also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the claimed subject matter may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media can include both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 10, the exemplary environment 1000 for implementing various aspects of the claimed subject matter includes a computer 1002, the computer 1002 including a processing unit 1004, a system memory 1006 and a system bus 1008. The system bus 1008 couples to system components including, but not limited to, the system memory 1006 to the processing unit 1004. The processing unit 1004 can be any of various commercially available processors. Dual microprocessors and other multi-processor architectures may also be employed as the processing unit 1004.

The system bus 1008 can be any of several types of bus structure that may further interconnect to a memory bus (with or without a memory controller), a peripheral bus, and a local bus using any of a variety of commercially available bus architectures. The system memory 1006 includes read-only memory (ROM) 1010 and random access memory (RAM) 1012. A basic input/output system (BIOS) is stored in a non-volatile memory 1010 such as ROM, EPROM, EEPROM, which BIOS contains the basic routines that help to transfer information between elements within the computer 1002, such as during start-up. The RAM 1012 can also include a high-speed RAM such as static RAM for caching data.

The computer 1002 further includes an internal hard disk drive (HDD) 1014 (e.g., EIDE, SATA), which internal hard disk drive 1014 may also be configured for external use in a suitable chassis (not shown), a magnetic floppy disk drive (FDD) 1016, (e.g., to read from or write to a removable diskette 1018) and an optical disk drive 1020, (e.g., reading a CD-ROM disk 1022 or, to read from or write to other high capacity optical media such as the DVD). The hard disk drive 1014, magnetic disk drive 1016 and optical disk drive 1020 can be connected to the system bus 1008 by a hard disk drive interface 1024, a magnetic disk drive interface 1026 and an optical drive interface 1028, respectively. The interface 1024 for external drive implementations includes at least one or both of Universal Serial Bus (USB) and IEEE1394 interface technologies. Other external drive connection technologies are within contemplation of the subject matter claimed herein.

The drives and their associated computer-readable media provide nonvolatile storage of data, data structures, computer-executable instructions, and so forth. For the computer 1002, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the claimed subject matter.

A number of program modules can be stored in the drives and RAM 1012, including an operating system 1030, one or more application programs 1032, other program modules 1034 and program data 1036. All or portions of the operating system, applications, modules, and/or data can also be cached in the RAM 1012. It is appreciated that the claimed subject matter can be implemented with various commercially available operating systems or combinations of operating systems.

A user can enter commands and information into the computer 1002 through one or more wired/wireless input devices, e.g. a keyboard 1038 and a pointing device, such as a mouse 1040. Other input devices (not shown) may include a microphone, an IR remote control, a joystick, a game pad, a stylus pen, touch screen, or the like. These and other input devices are often connected to the processing unit 1004 through an input device interface 1042 that is coupled to the system bus 1008, but can be connected by other interfaces, such as a parallel port, an IEEE1394 serial port, a game port, a USB port, an IR interface, etc.

A monitor 1044 or other type of display device is also connected to the system bus 1008 via an interface, such as a video adapter 1046. In addition to the monitor 1044, a computer typically includes other peripheral output devices (not shown), such as speakers, printers, etc.

The computer 1002 may operate in a networked environment using logical connections via wired and/or wireless communications to one or more remote computers, such as a remote computer(s) 1048. The remote computer(s) 1048 can be a workstation, a server computer, a router, a personal computer, a mobile device, portable computer, microprocessor-based entertainment appliance, a peer device or other common network node, and typically includes many or all of the elements described relative to the computer 1002, although, for purposes of brevity, only a memory/storage device 1050 is illustrated. The logical connections depicted include wired/wireless connectivity to a local area network (LAN) 1052 and/or larger networks, e.g. a wide area network (WAN) 1054. Such LAN and WAN networking environments are commonplace in offices and companies, and facilitate enterprise-wide computer networks, such as intranets, all of which may connect to a global communications network, e.g. the Internet.

When used in a LAN networking environment, the computer 1002 is connected to the local network 1052 through a wired and/or wireless communication network interface or adapter 1056. The adapter 1056 may facilitate wired or wireless communication to the LAN 1052, which may also include a wireless access point disposed thereon for communicating with the wireless adapter 1056.

When used in a WAN networking environment, the computer 1002 can include a modem 1058, or is connected to a communications server on the WAN 1054, or has other means for establishing communications over the WAN 1054, such as by way of the Internet. The modem 1058, which can be internal or external and a wired or wireless device, is connected to the system bus 1008 via the serial port interface 1042. In a networked environment, program modules depicted relative to the computer 1002, or portions thereof, can be stored in the remote memory/storage device 1050. It will be appreciated that the network connections shown are exemplary and other means of establishing a communications link between the computers can be used.

The computer 1002 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi, or Wireless Fidelity, allows connection to the Internet from a couch at home, a bed in a hotel room, or a conference room at work, without wires. Wi-Fi is a wireless technology similar to that used in a cell phone that enables such devices, e.g. computers, to send and receive data indoors and out; anywhere within the range of a base station. Wi-Fi networks use radio technologies called IEEE802.11 (a, b, g, n, etc.) to provide secure, reliable, fast wireless connectivity. A Wi-Fi network can be used to connect computers to each other, to the Internet, and to wired networks (which use IEEE802.3 or Ethernet). Wi-Fi networks operate in the unlicensed 2.4 and 5 GHz radio bands, at an 11 Mbps (802.11b) or 54 Mbps (802.11a) data rate, for example, or with products that contain both bands (dual band), so the networks can provide real-world performance similar to the basic "10BaseT" wired Ethernet networks used in many offices.

Figure 11:
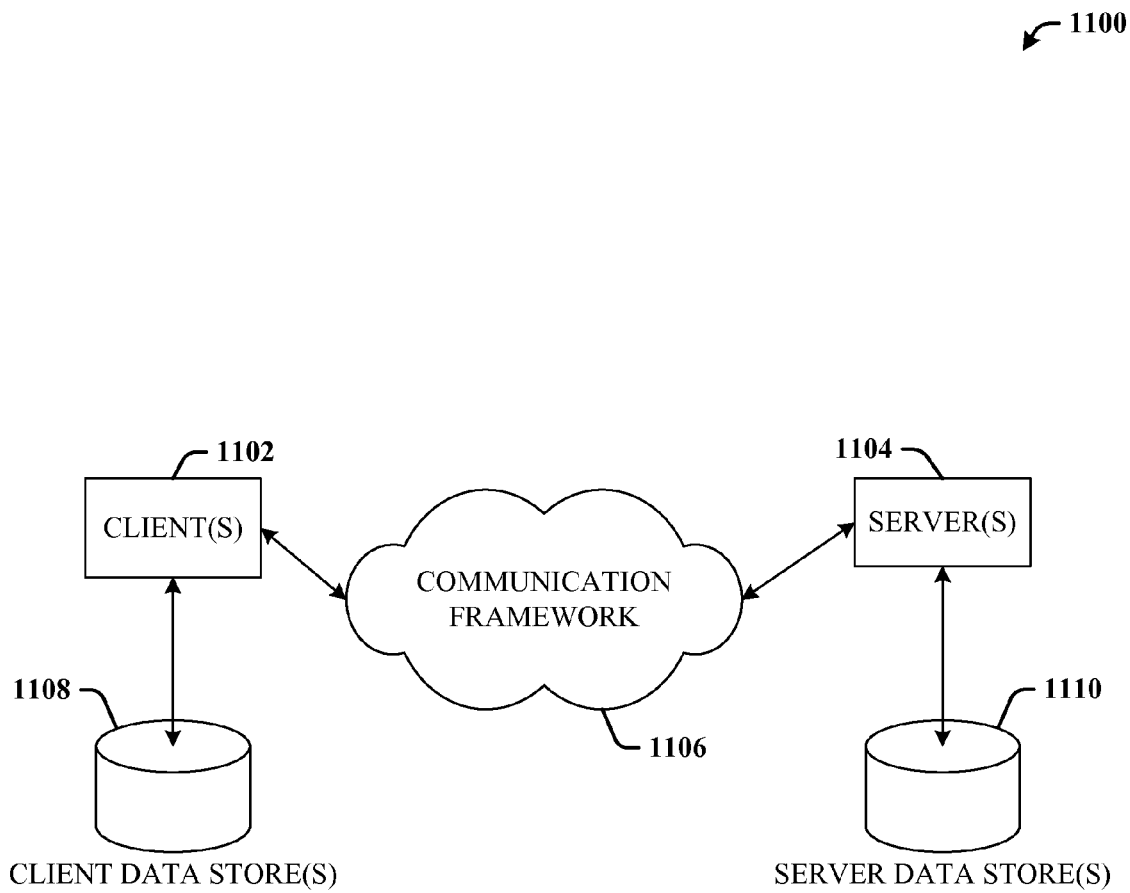
FIG. 11 illustrates a schematic block diagram of an exemplary computing environment.

Referring now to FIG. 11, there is illustrated a schematic block diagram of an exemplary computer compilation system operable to execute the disclosed architecture. The system 1100 includes one or more client(s) 1102. The client(s) 1102 can be hardware and/or software (e.g., threads, processes, computing devices). The client(s) 1102 can house cookie(s) and/or associated contextual information by employing the claimed subject matter, for example.

The system 1100 also includes one or more server(s) 1104. The server(s) 1104 can also be hardware and/or software (e.g., threads, processes, computing devices). The servers 1104 can house threads to perform transformations by employing the claimed subject matter, for example. One possible communication between a client 1102 and a server 1104 can be in the form of a data packet adapted to be transmitted between two or more computer processes. The data packet may include a cookie and/or associated contextual information, for example. The system 1100 includes a communication framework 1106 (e.g., a global communication network such as the Internet) that can be employed to facilitate communications between the client(s) 1102 and the server(s) 1104.

Communications can be facilitated via a wired (including optical fiber) and/or wireless technology. The client(s) 1102 are operatively connected to one or more client data store(s) 1108 that can be employed to store information local to the client(s) 1102 (e.g., cookie(s) and/or associated contextual information). Similarly, the server(s) 1104 are operatively connected to one or more server data store(s) 1110 that can be employed to store information local to the servers 1104.

What has been described above includes examples of the various embodiments. It is, of course, not possible to describe every conceivable combination of components or methodologies for purposes of describing the embodiments, but one of ordinary skill in the art may recognize that many further combinations and permutations are possible. Accordingly, the detailed description is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g. a functional equivalent), even though not structurally equivalent to the disclosed structure, which performs the function in the herein illustrated exemplary aspects of the embodiments. In this regard, it will also be recognized that the embodiments includes a system as well as a computer-readable medium having computer-executable instructions for performing the acts and/or events of the various methods.

In addition, while a particular feature may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. One or more computer storage media having a system embodied thereon including computer-executable instructions that, when executed, leverage a private affinity in order to facilitate or enrich relationships in a social network, the system comprising:
    a cryptography component that receives a social network user profile associated with a user who is a member of a social network, the social network user profile including a set of private affinities that are cryptographically protected from public inspection, each private affinity in the set of private affinities describing at least one of a like, preference, behavior, activity, or habit of the user, wherein protected from public inspection is defined by a degree of authorization that exceeds a level of authorization required to access the underlying social network user profile;
    a matching component that compares a private affinity from the set to a disparate affinity included in a disparate social network user profile associated with a disparate user in order to identify a matching affinity that correlates with the private affinity, the private affinity from the set being unknown to the disparate user; and
    a notification component that generates a message that indicates the matching affinity has been identified, the message including a request to publish to the disparate user revealed information included in the social network user profile.

2. The computer storage media of claim 1, wherein the social network user profile includes a public affinity that is accessible to public inspection, and wherein accessible to public inspection is defined by a degree of authorization that is substantially the same level of authorization required to access the underlying social network user profile.

3. The computer storage media of claim 1, wherein the matching affinity is a disparate public affinity that is accessible to public inspection or a disparate private affinity that is protected from public inspection; and wherein the matching affinity or the correlated private affinity to describes at least one of (1) a natural attraction of the user or a feeling of empathy or kinship to a person or thing by the user; or (2) a fringe interest of the user, an eccentricity of the user, or a domain of which the user is a part about which knowledge is not widely disseminated or not accurately understood or appreciated at large.

4. The computer storage media of claim 1, wherein the matching component compares the private affinity to the disparate affinity when the user and the disparate user exchange a user-inputted communication.

5. The computer storage media of claim 1, wherein the matching component compares the private affinity to the disparate affinity when the user and the disparate user are in close geographic proximity.

6. The computer storage media of claim 1, wherein the matching component identifies a matching affinity when the disparate affinity is substantially identical to the private affinity.

7. The computer storage media of claim 1, wherein the matching component identifies a matching affinity when the disparate affinity substantially complements the private affinity.

8. The computer storage media of claim 1, wherein the matching component identifies a matching affinity when the disparate affinity substantially conflicts with the private affinity.

9. The computer storage media of claim 1, wherein the revealed information is expressly authorized for sharing and comprises at least one of an identity of the user, a location of the user, or the private affinity; or wherein all or portions of the public data are reclassified as private data in connection with disseminating revealed information.

10. The computer storage media of claim 1, further comprising a negotiation component that brokers an exchange between the user and the disparate user.

11. The computer storage media of claim 10, wherein the negotiation component facilitates anonymous communication of user-inputted messages between the user and the disparate user.

12. The computer storage media of claim 10, wherein the negotiation component propagates the revealed information to the disparate user.

13. The computer storage media of claim 10, wherein the negotiation component propagates the revealed information to the disparate user only after a set of conditions are satisfied.

14. The computer storage media of claim 13, wherein the set of conditions includes at least one of a mutual exchange of revealed information or an existence of k-anonymity.

15. The computer storage media of claim 1, further comprising an advertising component that employs a peer-to-peer (P2P) ad model and that facilitates delivery of an advertisement to a disparate user device by way of a user device; or employs a correlation model to provide feedback to an advertiser.

16. The computer storage media of claim 15, wherein the advertisement or the feedback relates to the private affinity and wherein an incentive is provided to the user in exchange for delivering the advertisement or authorizing the feedback.

17. A computer-implemented method for utilizing hidden affinities for establishing or enhancing relationships, the method comprising:
    accessing a social network user profile associated with a user who is a member of a social network and a disparate social network user profile associated with a disparate user;
    retrieving from the social network user profile a private affinity from a set of private affinities relating to the user and that are concealed from third-party inspection, each private affinity in the set of private affinities describing at least one of a like, preference, behavior, activity, or habit of the user, wherein concealed from third-party inspection is defined by a level of authorization that exceeds authorization required to access the underlying social network user profile;

employing a processor for cryptographically comparing the private affinity to a disparate affinity included in the disparate social network user profile, the compared private affinity being unknown to the disparate user;

designating the disparate affinity as a matching affinity when the disparate affinity correlates with the private affinity;

requesting permission from the user for publishing to the disparate user revealed information included in the social network user profile.

18. The method of claim 17, further comprising at least one of the following acts:

comparing the private affinity to the disparate affinity when the user and the disparate user establish a history of communication;

comparing the private affinity to the disparate affinity when the user and the disparate user are substantially physically collocated;

designating the matching affinity when the disparate affinity is identical or substantially similar to the private affinity;

designating the matching affinity when the disparate affinity substantially complements the private affinity;

or designating the matching affinity when the disparate affinity substantially clashes with the private affinity.

19. The method of claim 17, further comprising at least one of the following acts:

including in the revealed information at least one of an identity, a location, the private affinity, or the matching affinity;

facilitating anonymous communication between the user and the disparate user;

requiring a set of conditions to be satisfied prior to transmitting the revealed information;

including in the set of conditions at least one of a condition of mutual exchange of revealed information or a condition associated with k-anonymity;

employing a P2P ad model for facilitating transmission of an advertisement from the user to the disparate user;

employing a correlation model for providing feedback to an advertiser; or providing an incentive to the user in exchange for delivering the advertisement to the disparate user or in exchange for authorizing the feedback to the advertiser.

20. One or more computer storage media having a system embodied thereon including computer-executable instructions that, when executed, facilitate dissemination of confidential information in connection with private affinities in order to establish or enrich relationships, the system comprising:

a cryptography component that receives a social network user profile associated with a user who is a member of a social network, the profile including a set of private affinities that are cryptographically protected from public inspection, each private affinity in the set of private affinities describing at least one of a like, preference, behavior, activity, or habit of the user, wherein protected from public inspection is defined by a degree of authorization that surpasses a level of authorization required to access the underlying social network user profile;

a matching component that compares a private affinity from the set to a disparate affinity included in a disparate social network user profile associated with a disparate user in order to identify a matching affinity that correlates with the private affinity, the private affinity from the set being unknown to the disparate user;

a notification component that generates a message that indicates the matching affinity has been identified, the message including a request to publish to the disparate user revealed information included in the social network user profile, wherein the revealed information is not available to the disparate user without express authorization from the user; and a negotiation component that facilitates sharing of revealed information upon satisfaction of a set of conditions including at least one of a condition of mutual exchange of revealed information or a condition of k-anonymity in connection with the revealed information.

* * * * *